US012697105B2

(12) United States Patent
Abrahams et al.

(10) Patent No.: US 12,697,105 B2
(45) Date of Patent: Aug. 4, 2026

(54) ANATOMICAL SPECIMEN COLLECTION DEVICE AND SYSTEM HAVING HIGH CAPACITY EXTENDED FILTERING CAPABILITY

(71) Applicant: Capseus, Inc., Ronkonkoma, NY (US)

(72) Inventors: John M. Abrahams, Scarsdale, NY (US); Michael R. Bielski, Manorville, NY (US); Don Hannula, San Luis Obispo, CA (US)

(73) Assignee: Capseus, Inc., Ronkonkoma, NY (US)

( * ) Notice: Subject to any disclaimer, the term of this patent is extended or adjusted under 35 U.S.C. 154(b) by 476 days.

(21) Appl. No.: 16/672,094

(22) Filed: Nov. 1, 2019

(65) Prior Publication Data

US 2020/0138417 A1     May 7, 2020

Related U.S. Application Data

(60) Provisional application No. 62/754,878, filed on Nov. 2, 2018.

(51) Int. Cl.
    *A61B 10/02*          (2006.01)
(52) U.S. Cl.
    CPC ........ *A61B 10/025* (2013.01); *A61B 10/0283* (2013.01)
(58) Field of Classification Search
    CPC .... A61B 10/0283; A61B 10/025; A61M 1/79; B01D 29/31; B01D 2201/00–0423; B01D 2201/30–306
    See application file for complete search history.

(56) References Cited

U.S. PATENT DOCUMENTS

| | | | | | |
|---|---|---|---|---|---|
| 3,224,434 | A | * | 12/1965 | Molomut | A61B 10/02 |
| | | | | | 433/91 |
| 4,615,694 | A | * | 10/1986 | Raines | A61M 5/165 |
| | | | | | 604/126 |
| 5,108,381 | A | * | 4/1992 | Kolozsi | A61B 10/02 |
| | | | | | 604/326 |
| 5,630,939 | A | * | 5/1997 | Bulard | B01D 35/02 |
| | | | | | 433/92 |
| 5,766,134 | A | * | 6/1998 | Lisak | A61B 10/025 |
| | | | | | 604/320 |
| 5,817,032 | A | * | 10/1998 | Williamson, IV | G01N 1/36 |
| | | | | | 604/319 |
| 6,299,763 | B1 | | 10/2001 | Ashman | |
| 8,915,921 | B2 | | 12/2014 | Ralph et al. | |
| 2006/0173426 | A1 | | 8/2006 | Urich et al. | |

(Continued)

OTHER PUBLICATIONS

International Search Report and Written Opinion dated Jan. 2, 2020 issued in corresponding International Application No. PCT/US2019/059472.

*Primary Examiner* — Jennifer Robertson
*Assistant Examiner* — H. Q. Nguyen
(74) *Attorney, Agent, or Firm* — Amster, Rothstein & Ebenstein LLP

(57)          ABSTRACT

An anatomical specimen collection device and system enabling a higher capacity, extended filtering capability and easy removal of the specimen while avoiding blockage or clogging. The anatomical specimen collection device includes a removable flexible nozzle with a distal end configured for mating with a variety of suction instruments and a removable axial filter element surrounded by a negative pressure environment.

16 Claims, 11 Drawing Sheets

(56) References Cited

U.S. PATENT DOCUMENTS

| | | | |
|---|---|---|---|
| 2008/0257815 A1 | 10/2008 | McCary | |
| 2008/0319345 A1 * | 12/2008 | Swenson .......... | A61B 5/150671 |
| | | | 600/576 |
| 2009/0306669 A1 | 12/2009 | Takahashi | |
| 2014/0316357 A1 * | 10/2014 | Adams .................... | A61M 1/74 |
| | | | 604/319 |
| 2017/0202579 A1 * | 7/2017 | Abrahams ............. | A61M 1/743 |

* cited by examiner

SECTION B-B

6

ANATOMICAL SPECIMEN COLLECTION DEVICE AND SYSTEM HAVING HIGH CAPACITY EXTENDED FILTERING CAPABILITY

CROSS-REFERENCE TO RELATED APPLICATIONS

The present application claims benefit of and priority to U.S. Provisional Patent Application No. 62/754,878 filed Nov. 2, 2018 entitled ANATOMICAL SPECIMEN COLLECTION DEVICE AND SYSTEM HAVING HIGH CAPACITY EXTENDED FILTERING CAPABILITY, and relates to International Application Number PCT/US2015/042017 by J. Abrahams et al., filed on Jul. 24, 2015, published as WO 2016/014955 A1 entitled ANATOMICAL SPECIMEN COLLECTION DEVICE AND SYSTEM, the entire contents of which is incorporated by reference herein.

BACKGROUND

1. Technical Field

The present disclosure relates to anatomical specimen collection device and systems. In particular, the present disclosure relates to a device for collecting bone dust that is suitable for use with conventional operating room suction devices and includes a removable flexible nozzle with a distal end configured for mating with a variety of suction instruments and a removable axial filter element surrounded by a negative pressure environment.

2. Related Art

Devices for harvesting anatomical specimens such as bone dust from a subject and replacing the anatomical specimen in the subject are known in the art. Existing devices, however, suffer from several deficiencies that make them difficult and inefficient to use. In some existing systems, the desired specimen is mixed with other materials such as blood, saline and other tissue and must undergo a separate processing procedure to remove these unwanted materials. For example, in some conventional bone collecting devices and systems, bone dust and materials are stored in a container and mixed together. In order to separate the desired bone dust from the other material, the combined materials are compressed using a press to force the liquid out and leave the bone behind. These additional steps are inefficient and may damage the desired specimen material. In some existing systems, the collections apparatus is large and awkward and interferes with the physician's ability to properly perform the procedure. In other existing systems, removal of the desired specimen, even if properly separated, is cumbersome and may damage the specimen. In still other systems, collection of the desired specimen leads to blockage or clogging which requires frequent breaks to prematurely empty and clear the specimen storage area.

Accordingly, it would be desirable to provide an anatomical specimen collection device and system, such as a bone dust collecting device and system that avoids these and other problems.

SUMMARY

The present disclosure relates to an anatomical specimen collection device and system enabling a higher capacity, extended filtering capability and easy removal of the specimen while avoiding blockage or clogging.

An anatomical specimen collection device in accordance with an embodiment of the present disclosure includes: a hollow body extending along a longitudinal axis; the body including: a first opening in a proximal end thereof, the first opening surrounded by a flange extending in the proximal direction and including a plurality of stepped protrusions on an outer surface thereof; and a second opening at a distal end thereof; a filter mounted in the body between the first opening and the second opening: the filter including: a closed proximal end portion; an open distal end portion; and a mesh portion extending longitudinally between the closed proximal end portion and the open distal end portion defining an interior space aligned with the longitudinal axis; and a flexible nozzle removably connected to the distal end of the body, the flexible nozzle tapering from a proximal end thereof in contact with the body to a distal end thereof, the distal end including a suction opening that is in fluid communication with the interior space of the filter and the first opening in the proximal end of the body such that anatomical specimen material is drawn into the suction opening, through the filter and the first opening when the first opening is connected to suction.

In embodiments, the mesh portion includes a mesh with a plurality of openings that are sized to allow blood and saline to pass through, while preventing bone dust from passing.

In embodiments, the filter further comprises a cylindrical support element at the open distal end thereof.

In embodiments, the body further includes two opposed wall extensions between which the cylindrical support element of the filter is received, the wall extensions are spaced apart from each other such that at least one gap is formed to allow access to the cylindrical support element.

In embodiments, the filter further comprises two opposed ribs extending from the cylindrical support element to the closed proximal end of the filter and supporting the mesh of the mesh portion.

In embodiments, the filter is positioned such that there is a first gap between an outer perimeter of the filter and an internal surface of the body and a second gap between the closed proximal end portion of the filter and the proximal end of the body such that the first gap and the second gap are subject to negative pressure when the first opening of the body is connected to suction.

In embodiments, the body further comprises at least one raised protrusion formed on an outer surface of the distal end thereof.

In embodiments, an inner surface of the proximal end of the nozzle includes at least one channel positioned and configured to receive the at least one raised protrusion of the body to secure the nozzle to the body.

In embodiments, the nozzle is made of a flexible silicone material that is approved for contact with a patient's body.

In embodiments, the body further includes a vent opening formed in an outer surface of the body near the distal end thereof.

In embodiments, an interior surface of the nozzle is substantially flat such that anatomical specimens flow easily through the nozzle to the filter.

In embodiments, the suction opening of the nozzle has a smaller diameter than the proximal end of the nozzle.

In embodiments, the suction opening is flexible.

An anatomical specimen collection system in accordance with an embodiment of the present disclosure includes a suction tube configured for connection to a suction supply;

and an anatomical specimen collection device in fluid communication with the section tube, the anatomical specimen collection device including: a hollow body extending along a longitudinal axis; the body including: a first opening in a proximal end thereof, the first opening surrounded by a flange extending in the proximal direction and including a plurality of stepped protrusions on an outer surface thereof; and a second opening at a distal end thereof; a filter mounted in the body between the first opening and the second opening: the filter including: a closed proximal end portion; an open distal end portion; and a mesh portion extending longitudinally between the closed proximal end portion and the open distal end portion defining an interior space aligned with the longitudinal axis; and a flexible nozzle removably connected to the distal end of the body, the flexible nozzle tapering from a proximal end thereof in contact with the body to a distal end thereof, the distal end including a suction opening that is in fluid communication with the interior space of the filter and the first opening in the proximal end of the body such that anatomical specimen material is drawn into the suction opening, through the filter and the first opening when suction is applied via the suction hose through the first opening.

In embodiments, the anatomical specimen collection system includes a hollow suction instrument connected to the suction opening of the nozzle and including a distal end configured for contact with a patient to provide anatomical specimen material to the anatomical specimen collection device.

In embodiments, the proximal end of the hollow suction instrument includes a stepped outer surface that is received in the suction opening of the anatomical specimen collection device to connect the instrument to the anatomical specimen collection device.

In embodiments, an interior surface of the suction opening is substantially smooth such that anatomical specimen material flows freely into the anatomical specimen collection device.

In embodiments, the hollow suction instrument is one of a Frazier instrument, a Poole instrument, and a Yankauer instrument.

In embodiments, the anatomical specimen collection system includes: an adaptor element including a proximal end that is received in the suction opening of the nozzle; and a distal end; and a second suction hose with a proximal end connected to the distal end of the adaptor and a distal end connected to a hollow suction instrument such that anatomical specimen material is collected by the hollow suction instrument and passes through the second suction hose, through the adaptor element and into the anatomical specimen collection device through the suction opening.

In embodiments, the hollow suction instrument is one of a Frazier instrument, a Poole instrument, and a Yankauer instrument.

BRIEF DESCRIPTION OF THE DRAWINGS

The above and related objects, features and advantages of the present disclosure will be more fully understood by reference to the following detailed description of the preferred, albeit illustrative, embodiments of the present invention when taken in conjunction with the accompanying figures, wherein.

DETAILED DESCRIPTION OF THE EMBODIMENTS

As defined herein, proximal end refers to an end of the anatomical specimen collection device or anatomical specimen collection system that is closest to the user or to an operating room suction source connection.

Distal end refers to an end of the anatomical specimen collection device or anatomical specimen collection system that is furthest from the user or from an operating room suction source connection.

In the figures that are described below, specific numerical dimensions may be illustrated and are merely examples of numerical values of those dimensions. Such numerical dimensions may be varied as desired or otherwise deemed necessary for application of the bone collection device or anatomical specimen collection system to its intended usage.

Figure 1:
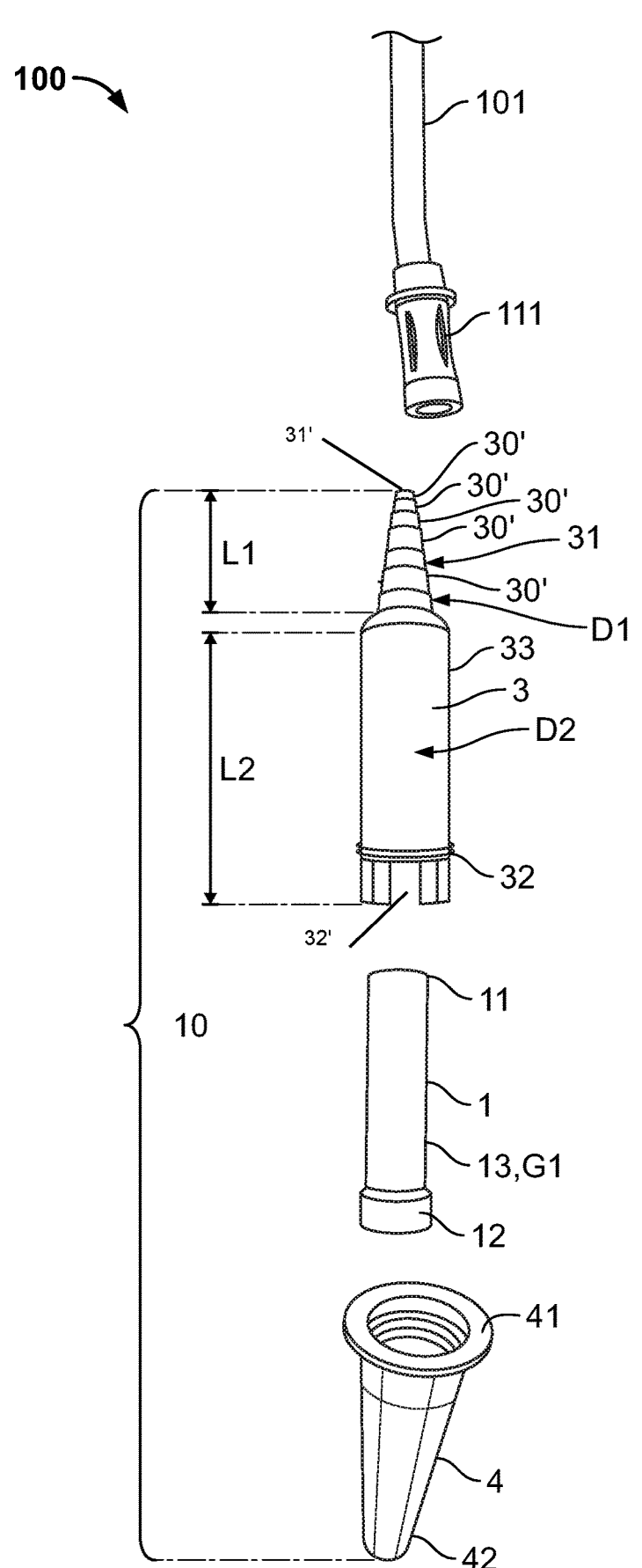
FIG. 1 is an exploded view of an anatomical specimen collection system in accordance with an embodiment of the present disclosure.

FIG. 1 illustrates an exploded view of an anatomical specimen collection system 100 including an anatomical specimen collection device 10 according to an embodiment of the present disclosure.

More particularly, in embodiments, the anatomical specimen collection device 10 my include a tubular body 3 having a proximal end portion 31 and a distal end portion 32, wherein the tubular body 3 defines a longitudinal axis X-X. In embodiments, the body 3 includes a minor opening 31' at proximal end 31 to a first internal volume of space 35' in the proximal end portion 31. In embodiments, a major opening 32' may be provided at a distal end portion 32 that opens to a second internal volume of space 35". In embodiments, the tubular body 3 may be configured in the form of a funnel shape wherein the proximal end portion 31 extends distally over a length L1 to a transition region 33 wherein internal diameter D1 of the proximal end portion 31 expands or flares outwardly to internal diameter D2 and the distal end portion 32 extends distally over a length L2. In embodiments, the external surface 30 of the proximal end portion 31 is configured over the length L1 with a series of progressively larger diameter stepped connectors 30' that increase in diameter from the proximal end toward the distal end towards the location of the internal diameter D2. In embodiments, the progressively larger diameter stepped connectors 30' thus allow connection to a variety of operation room suction line diameters such as operating room suction source line 101 that includes a connector 111 having an opening 112 in which the proximal portion 31 is received. In embodiments, the stepped connectors 30' allow direct connection to a variety of operating room suction line tube sizes that may be available to the user such that they provide for an integral "universal connector" in the device 10.

In embodiments, the major opening 32' may be configured to receive a cylindrical basket filter 1. In embodiments, the filter 1 may include a proximal end portion 11 and a distal end portion 12 such that the cylindrical basket filter 1 is configured to align with longitudinal axis X-X of the body 3. In embodiments, the proximal end portion 11 may be inserted into the major orifice 32' of the body 3 wherein the filter 1 extends generally over the length L2 of the distal end portion 32 of the tubular body 3. In embodiments, a clearance gap G1 may be defined between the perimeter 13 of the cylindrical basket filter 1 and internal body surface 34. In embodiments, the cylindrical basket filter 1 includes a filter mesh portion 14 that is maintained in an extended cylindrical position by first and second alignment ribs 15a and 15b that are parallel to one another and extend orthogonally from a toroidal surface 16' of cylindrical supporting structure 16. In embodiments, the filter mesh 14 includes a closed end 14' on the proximal end thereof. In embodiments, the filter mesh 14 includes an open end 14" including cylindrical end supporting structure 16 to define a distal open end 16" through which bone dust or other anatomical specimens are suctioned into the cylindrical basket filter 1 during operation of the device 10.

Figure 2:
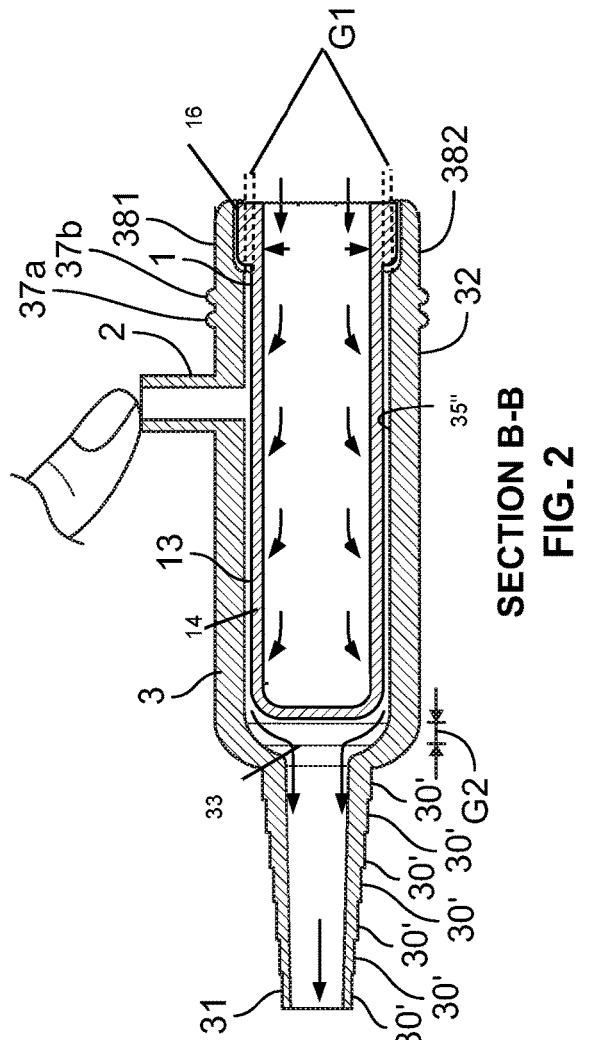
FIG. 2 is a cross-sectional view of a body of an anatomical specimen collection device included in the anatomical specimen collection system of FIG. 1 in accordance with an embodiment of the present disclosure.
Figure 3:
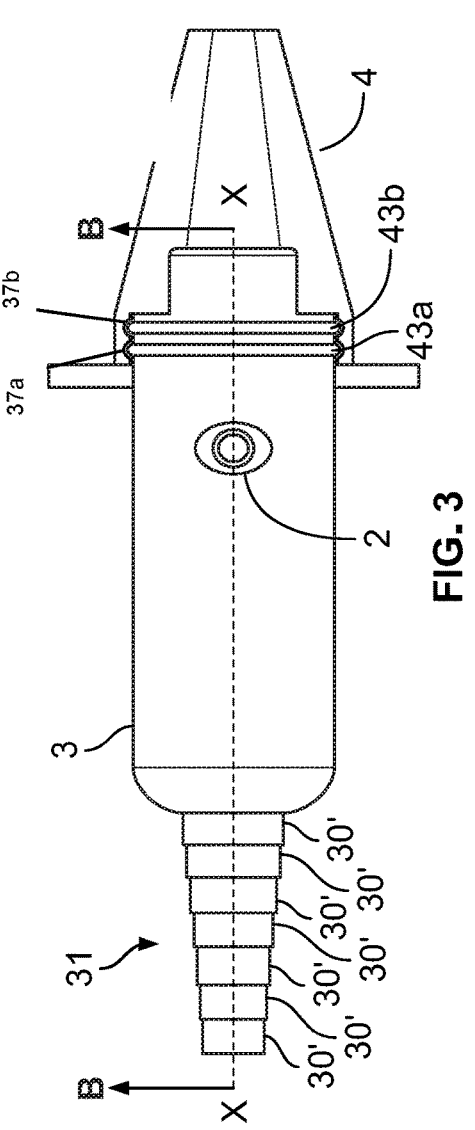
FIG. 3 is a more detailed top view of the body of the anatomical specimen collection device of FIG. 2 in accordance with an embodiment of the present disclosure.

In embodiments, the proximal closed end 14' of the mesh portion 14 is received within the second internal volume of space 35" along length L2 to form a clearance gap G2 (see FIG. 2, for example) between the proximal closed end 14' of the filter mesh portion 14 and the interior of the flared transition region 33 of the proximal end portion 31 of the body 3. In embodiments, since the mesh portion 14 is positioned in the space 35", it is surrounded by negative pressure such that liquid is drawn through the mesh on all sides. This increased surface area subject to suction and reduces the chances of a clog in the filter 1.

In embodiments, the body 3 may include a port opening 23 in cylindrical wall 36 that enables fluidic communication with the ambient air to the first and second internal volumes of space 35' and 35". In embodiments, covering and uncovering the opening 23 may be used to control suction through the device 10.

In embodiment, the distal end portion 32 of body 3 includes at least two spaced apart sequential projections 37a, 37b and at the extreme distal end of body wall 36 and distal from the projections 37a, 37b, partial wall extensions 381 and 382 that define a gap 39 that enables a user to grasp the cylindrical end supporting structure 16 of the filter 1 and insert or withdraw the filter mesh 14 into or from the second internal volume of space 35" in the body 3. In embodiments, following usage of the device 10, the gap 39 allows a user to easily grasp the cylindrical end supporting structure 16 if the filter and remove it from the body 3. Easy removal of the filer improves efficiency of the device 10 and the system and reduces the likelihood that the collected specimen will be damaged.

In embodiments, the anatomical specimen collection device 10 includes a flexible nozzle 4 having a proximal end portion 41 that is attached to the distal portion of the body 3 and distal end part 42. In embodiments, the inner surface 41' of the proximal end portion 41 of the nozzle 4 includes at least two spaced apart sequential channels 43a, 43b that are configured to receive the spaced apart sequential projections 37a, 37b formed on the body 3 so as to seal the nozzle 4 to the body 3. In embodiments, the lumen of the nozzle 4 increases in width in the proximal direction from the tip at distal end portion 42 to the body attachment part of the proximal end portion 41 thereof. In embodiment, this increase in the lumen diameter ensures that the inner lumen is less likely to plug during collection as it widens on the downstream side. In embodiments, the internal diameter where the body 3 is connected to the nozzle 4 provides a smooth transition from the nozzle 4 to the body 3 so that there are no shelves or obstacles that initiate clogging of the device 10. In embodiments, the body 3 and the nozzle 4 may be connected using other connecting structures. In embodiments, the projections 37a, 37b may be one or more threads and the interior of the nozzle 4 may include one or more matching threads such that the nozzle 4 may be screwed into the body 3. In such an embodiment, the nozzle 4 may be made of a molded silica or other material, if desired. In embodiments, a seal may be provided between the nozzle 4 and the body 3 to prevent leakage of air or fluid from the volumes 35', 35".

In embodiments, the nozzle 4 is preferably made of a silicone material. In embodiments, the silicone material selected for the nozzle 4 is selected to avoid adhesion with the collected tissue, as silicone does not attach to other non-silicone materials. In embodiments the silicone material used in the nozzle is safe for contact with a patient's skin or other part of the patient's anatomy.

In embodiments, following insertion of the mesh portion 14 of the filter 1 into the internal volume of space 35' of the body 3, the nozzle 4 may be installed by the user onto the body 3 such that the channels 43a, 43b receive the thread projections 37a, 37b, respectively. In embodiments, the sequential, spaced apart configuration of the channels 43a, 43*b* and thread projections 37*a*, 37*b* provides a secure attachment of the nozzle 4 to the body 3 to minimize the chances of inadvertent separation of the nozzle 4 from the body 3 and to maintain proper suction pressure during usage. In embodiments, the flexible nozzle 4 generally aligns with the longitudinal axis X-X of the body 3 and the filter 1. In embodiments, the flexible nature of the silicone nozzle 4 and the interaction between the channels 43*a*, 43*b* and the projections 37*a*, 37*b* results in a connection between the nozzle and the housing that resists separations when the nozzle and body are pulled in opposite directions but allows for relatively easy separation where the nozzle is pulled in a transverse direction relative to the axis of the body 3.

In embodiments, the design of the body 3 allows for easy intuitive placement of the nozzle 4 with tactile and visual feedback of engagement of each with respect to the other. In embodiments, the nozzle 4 and body 3 engagement features are designed such that assembly is easy provides retention during use, yet allows for easy removal upon demand. In embodiments, the flexible nature of the silicone nozzle 4 and the interaction between the channels 43*a*, 43*b* and the projections 37*a*, 37*b* results in a connection between the nozzle and the housing that resists separations when the nozzle and body are pulled in opposite directions but allows for relatively easy separation where the nozzle is pulled in a transverse direction relative to the axis of the body 3 to peel the nozzle away from the body.

In embodiments, the design of the body 3 also allows for easy and intuitive insertion and removal of the filter 1 by the user. In embodiments, the body 3 has finger clearance areas that allow direct easy contact of toroidal surface 16' of cylindrical end supporting structure 16 allowing easy removal of the filter 1 from the body 3. In embodiments, the filter 1 and body 3 are structured to ensure proper sealing in order to ensure maximum efficiency of collection of bone dust and maximum passing of all fluid content.

In embodiments, the body 3 may be semi-translucent to provide visibility of the collected tissue as a means of visual feedback to the user during use of the device 10.

The anatomical specimen collection device 10 may be used to collect bone dust or other anatomical specimen in a variety of ways. The device 10 is generally connected with an operating room suction tube 101 via adapter 111 and paired with a suction instrument connected to the distal end of the nozzle 4 to provide anatomical specimen collection system.

Figures 4, 5:
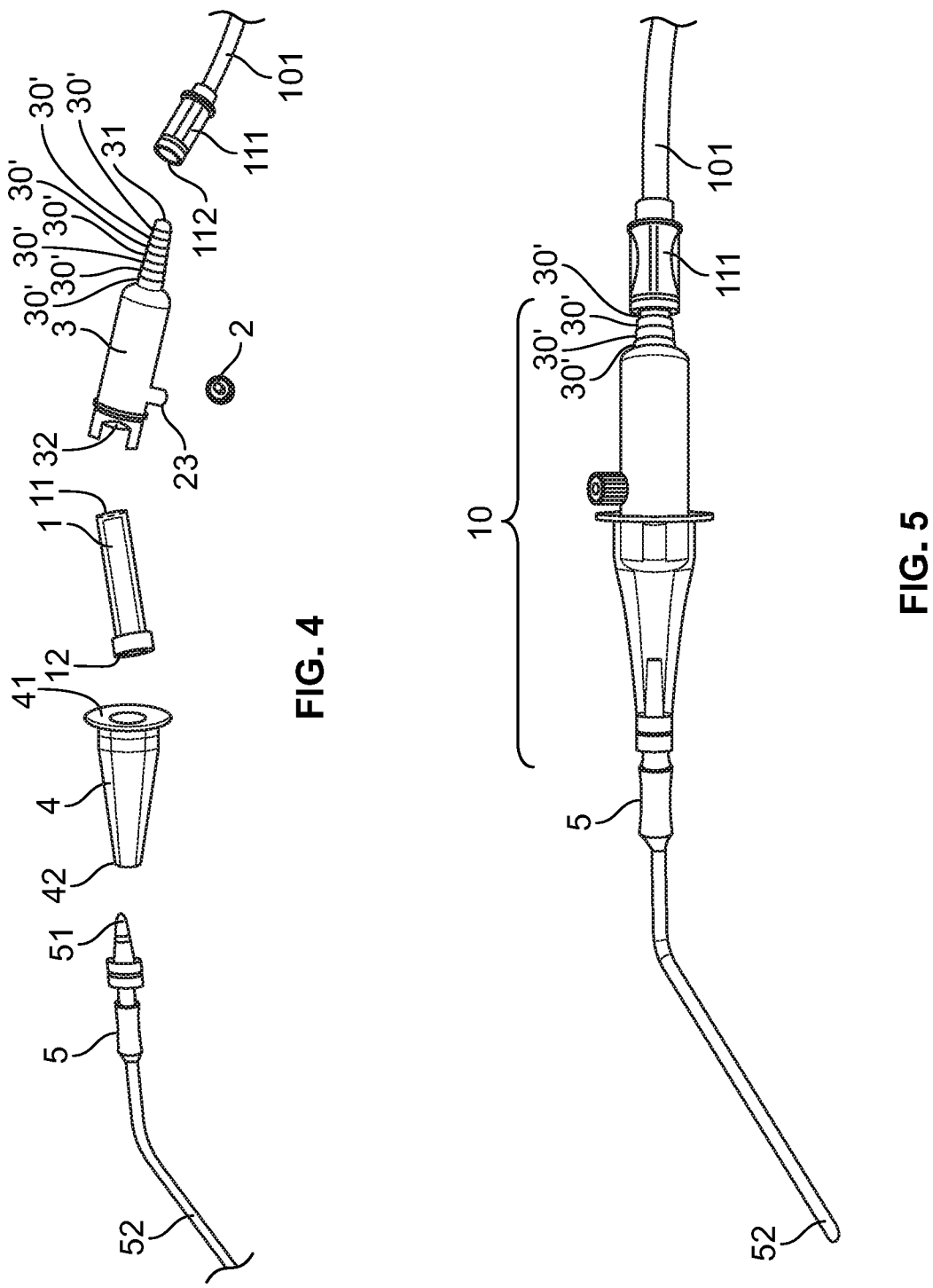
FIG. 4 is an exploded view of an anatomical specimen collection system including a Frazier suction instrument in accordance with an embodiment of the present disclosure.
FIG. 5 illustrates the anatomical specimen collection system of FIG. 4 in accordance with an embodiment of the present disclosure.

FIG. 4 illustrates an exploded view of an optional system 200 in an arrangement commonly known in the art as a Frazier set-up as it uses a Frazier suction instrument 5.

In this embodiment, an operating room suction source line 101 includes a connector 111 having an orifice 112. The proximal end portion 31 with minor opening 31' to first internal volume of space 35' is inserted into the orifice 112 of the connector 111 such that there is fluid communication between the line 101 and the space 35'.

A Frazier surgical suction instrument 5 may include a proximal end portion 51 having an orifice in fluid communication with an internal conduit that extends to distal tip 52 where anatomical specimens such as bone dust are collected from the patient. In embodiments, the Frazier instrument 5 contacts the patient and is connected to the nozzle 4 of the device 10.

In embodiments, the proximal end portion 51 of the Frazier instrument 5 may be received in the distal end portion 42 of the nozzle 4 to establish fluidic communication with the operating room suction source line 101 through the anatomical specimen collection device 10.

In operation, a Luer cap 2 may be placed over the port opening 23 in cylindrical wall 36 of the body 3 to seal the device 10 from the ambient air. In embodiments, suction through the device 10 may be controlled by the user by placing a finger over an orifice in the Frazier surgical suction instrument 5.

In embodiments, upon completion of the anatomical collection procedure, the user may disconnect the operating room suction source line 101 and the Frazier surgical suction instrument 5 from the device 10 and the bone dust or other sample is removed from the device 10 as explained above.

As previously indicated above, in embodiments, the sequential, spaced apart configuration of the channels 43*a*, 43*b* and thread projections 37*a*, 37*b* provides a secure method of attaching the nozzle 4 to the body 3 to minimize inadvertent separation of the nozzle 4 from the body 3 and to maintain proper suction pressure during usage. The secure connection provided by the configuration of the channels 43*a*, 43*b* and projections 37*a*, 37*b* also reduces the chances that the nozzle 4 will become separated from the body 3 when the Frazier surgical suction instrument 5 is installed onto the nozzle tip at distal end portion 42 of the nozzle 42.

Figure 6:
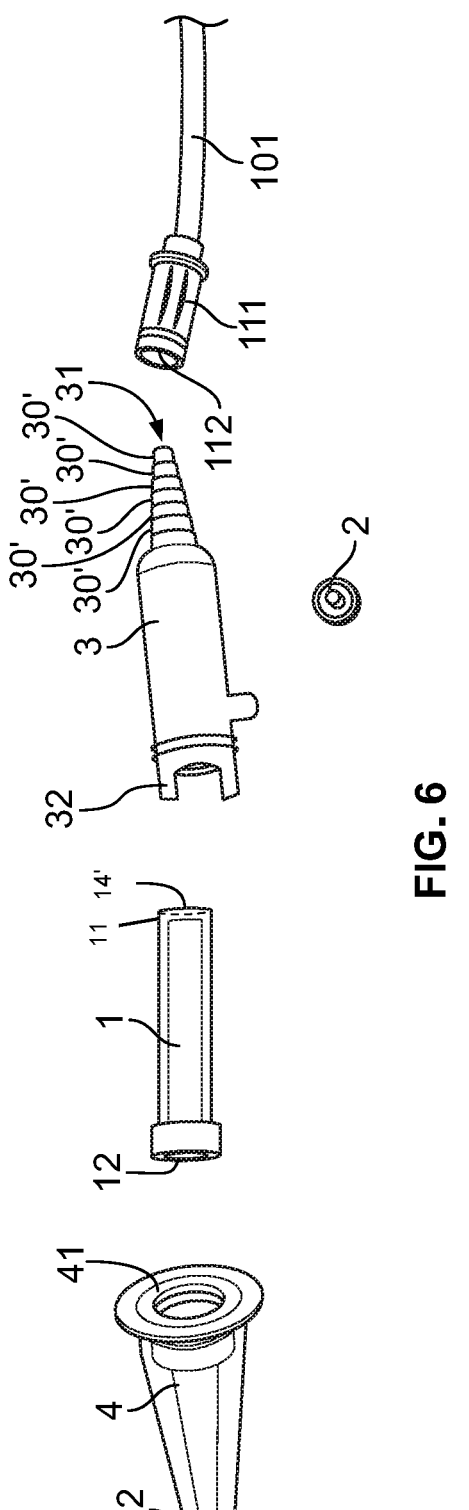
FIG. 6 is another exploded view of the anatomical specimen collection system of FIG. 1 in accordance with an embodiment of the present disclosure.
Figure 7:
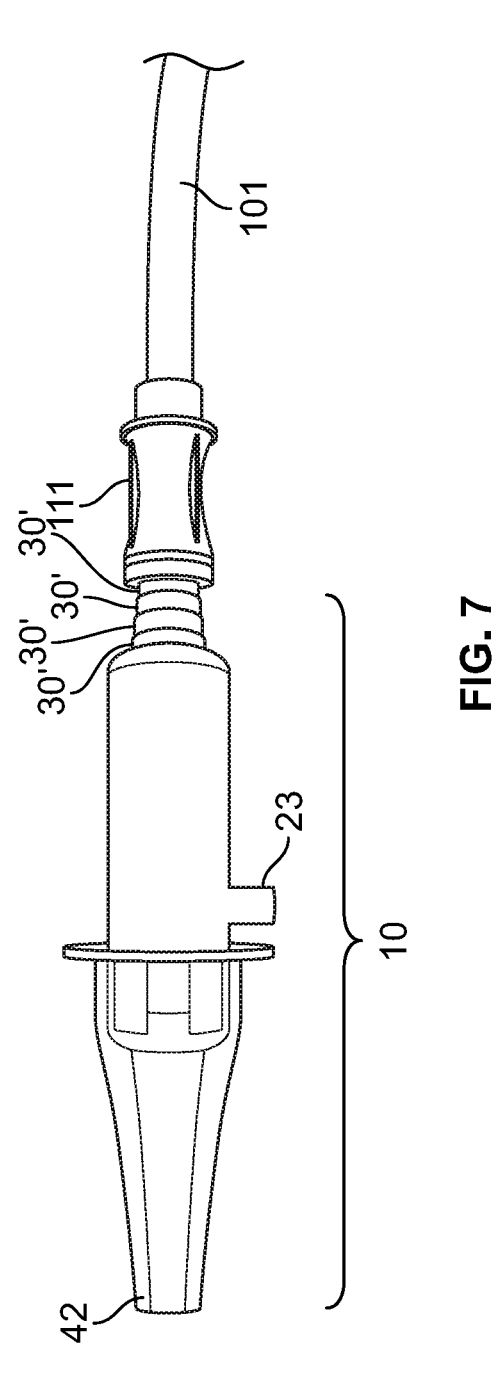
FIG. 7 illustrates the anatomical specimen collection system of FIG. 6 in accordance with an embodiment of the present disclosure.

In another embodiment, the operating room suction source line 101 may be connected to the minor opening orifice 31' of the proximal end portion 31 of the body 3 as before but collection of the bone dust or other sample is performed directly via the distal end portion 42 of the nozzle 4 as can be seen in the system 100 of FIGS. 1 and 6-7. In embodiments, suction pressure may be controlled by the user by placing his or her finger over the port opening 23 in cylindrical wall 36 of the body 3. In this embodiment, the Luer cap 2 may not be used to allow for finger control. In embodiments, when the nozzle 4 is used to collect the tissue or bone dust specimen without a Frazier or other instrument, the side port 23 (without a Luer cap) is used by the surgeon to regulate suction at the tip 42 of the nozzle 4 by plugging the side port 23 with the thumb or other finger in order to engage/disengage suction.

In embodiments, upon completion of the procedure, the device 10 may simply be disconnected from the operating room suction source line 101 and the bone dust or other anatomical sample retained in the filter 1 may be removed from the device as indicated previously.

Figures 8, 9:
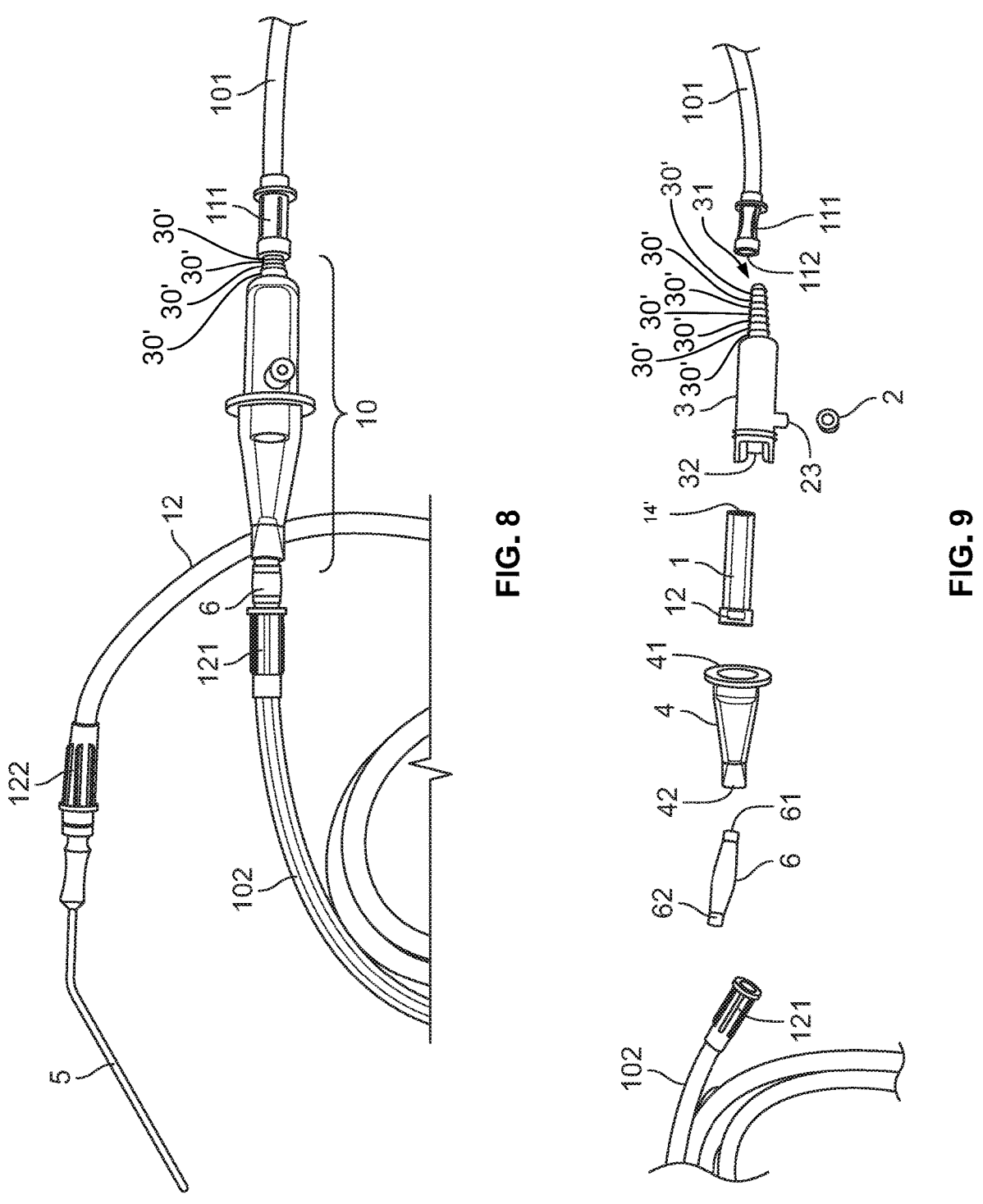
FIG. 8 illustrates an anatomical specimen collection system in which the anatomical specimen collection device is moved to a downstream position, further away from the patient in accordance with an embodiment of the present disclosure.
FIG. 9 illustrates an exploded view of the anatomical specimen collection system of FIG. 8 in accordance with an embodiment of the present disclosure.

FIGS. 8-9 illustrate an alternate system 300 that uses the device 10. In embodiments, the system 300 uses an in-line suction setup wherein the operating room suction source line 101 is connected to the minor orifice 31' of the proximal end portion 31 of the body 3 as before but instead of the Frazier surgical suction instrument 5 being connected to the distal end portion 42 of the nozzle 4, a dual male end suction connection adapter 6 having a proximal end portion 61 and a distal end portion 62 is installed between the distal end portion 42 of the nozzle 4 and an in-line suction tube 102. In this system, the device 10 is positioned well downstream of the patient but still in-line with the operating room suction.

In embodiments, the proximal end portion 61 of the adapter 6 is inserted into the distal end portion 42 of the nozzle 4 while the distal end portion 62 of the adapter 6 is inserted into a flexible suction line 102 having a proximal inlet connector 121 and a distal outlet connector 122.

In embodiments, the proximal end portion 51 of the Frazier surgical suction instrument 5 may be inserted into the distal outlet connector 122 of the flexible suction line 102, thereby established fluidic communication between the Frazier surgical suction instrument 5 and the operating room suction line 101 through the flexible suction line 102 and the device 10.

In embodiments, a Luer cap 2 may be placed over the port opening 23 in cylindrical wall 36 of the body 3 to seal the device 10 from the ambient air and vacuum is controlled by the user by placing a finger over an orifice in the Frazier surgical suction instrument 5. In embodiments, the port opening 23 may be eliminated altogether from the body 3.

With respect to each of the systems 100, 200 and 300, the gap 39 facilitates grasping of the filter 1 for removal and replacement of the filter when the filter is completely filled and also enables the device 10 to continue collecting bone dust or other anatomical specimens while the filter is being removed.

In embodiments, it may not be necessary to disconnect the device 10 from the operating room suction line 101 or to remove the Frazier surgical suction instrument 5 to remove the filter 1. In embodiments, the nozzle 4 may be removed (with the Frazier surgical suction instrument 50 still attached) thereby exposing the gap 39. The exposure of the gap 39 then allows the user to grasp the filter 1 and remove it from the body 3. In embodiments, a new filter may be inserted and the nozzle 4 can be replaced and more collection can occur (if necessary). In embodiments, the filter 1 may be removed, cleaned to collect the specimen and replaced in the device 10 to collect more specimen material.

In addition, in embodiments, a user, such as a surgeon may disconnect the entire device 10 from the operating room suction line 101 and transfer the device 10 to another user such as a technician, who may then remove the nozzle 4, remove the basket filter 1, replace the basket 1, then reinstall the nozzle 4 onto the body 3 as described above and transfer the device back to the surgeon to be attached back to the operating room suction line 101. Those skilled in the art will recognize there are multiple methods of using the device 10 to maintain workflow in the operating room.

In embodiments, more than two thread projections 37a, 37b may be included on the body 3 and more than two channels 43a, 43b may be provided in the inner surface of the nozzle 4. In embodiments, fewer channels and projections may also be used.

Figure 10:
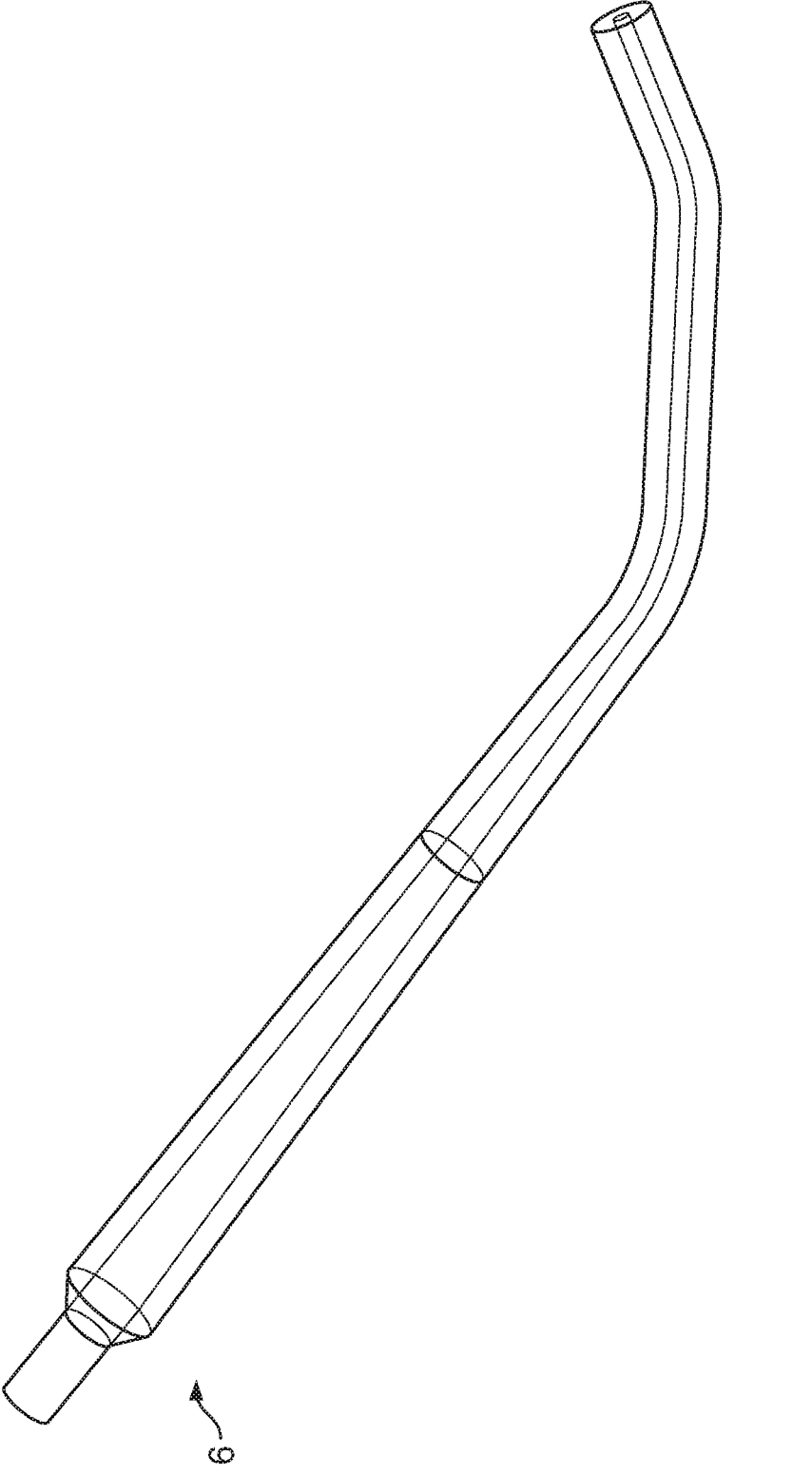
FIG. 10 illustrate an exemplary embodiment of an Yankauer suction instrument suitable for use with an anatomical specimen collection system in accordance with an embodiment of the present disclosure.

FIG. 10 illustrates an example of a Yankauer suction instrument 6 that may be used in place of the Frazier instrument 5 discussed above in any of the systems 100, 200, 300.

Figures 11, 12A, 12B, 13:
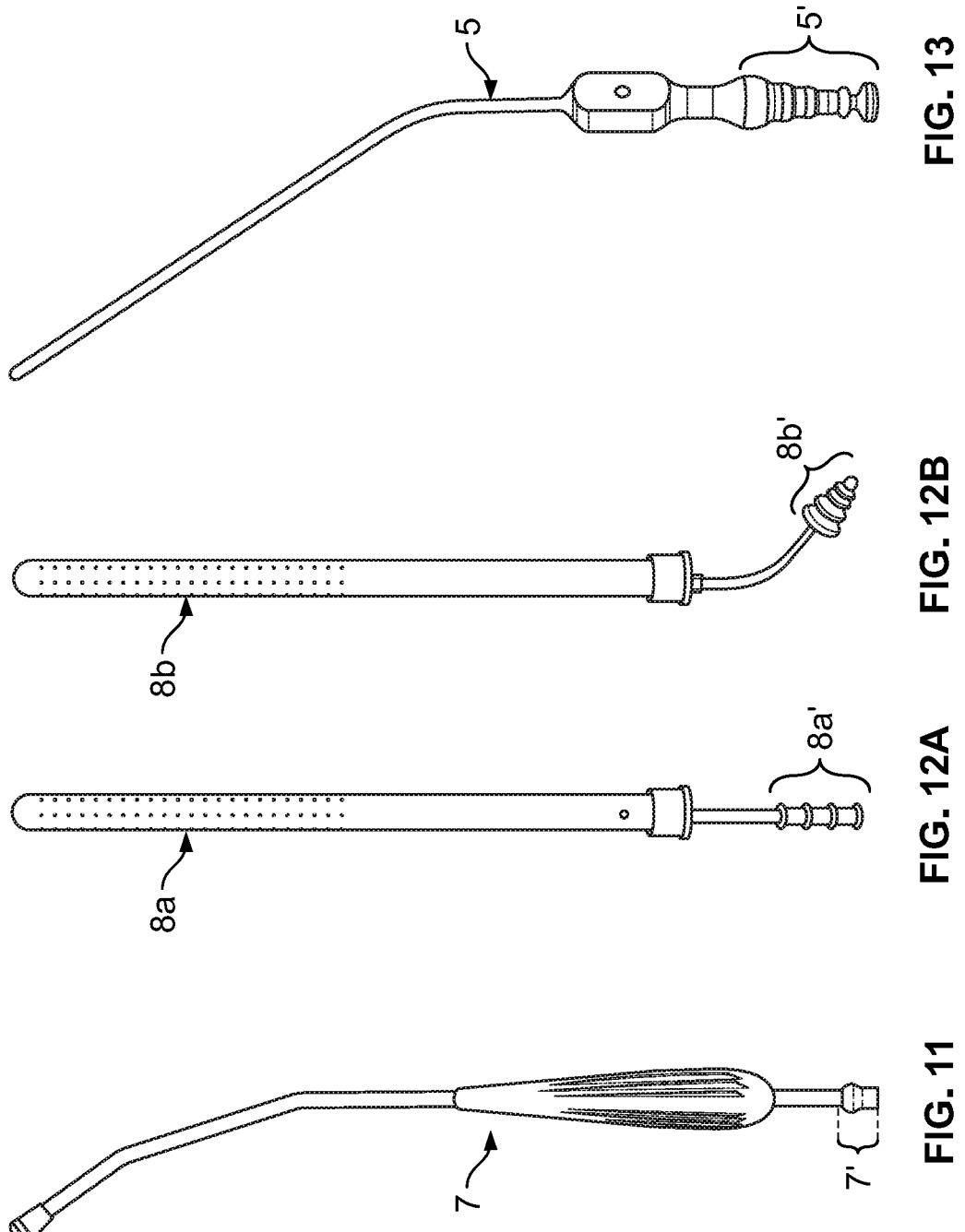
FIG. 11 illustrates another exemplary embodiment of an Yankauer suction instrument suitable for use with an anatomical specimen collection system in accordance with an embodiment of the present disclosure.
FIGS. 12A and 12B illustrate examples of Poole suction instruments suitable for use with an anatomical specimen collection system in accordance with an embodiment of the present disclosure.
FIG. 13 illustrates an example of a Frazier suction instrument suitable for use with an anatomical specimen collection system in accordance with an embodiment of the present disclosure.
Figure 14:
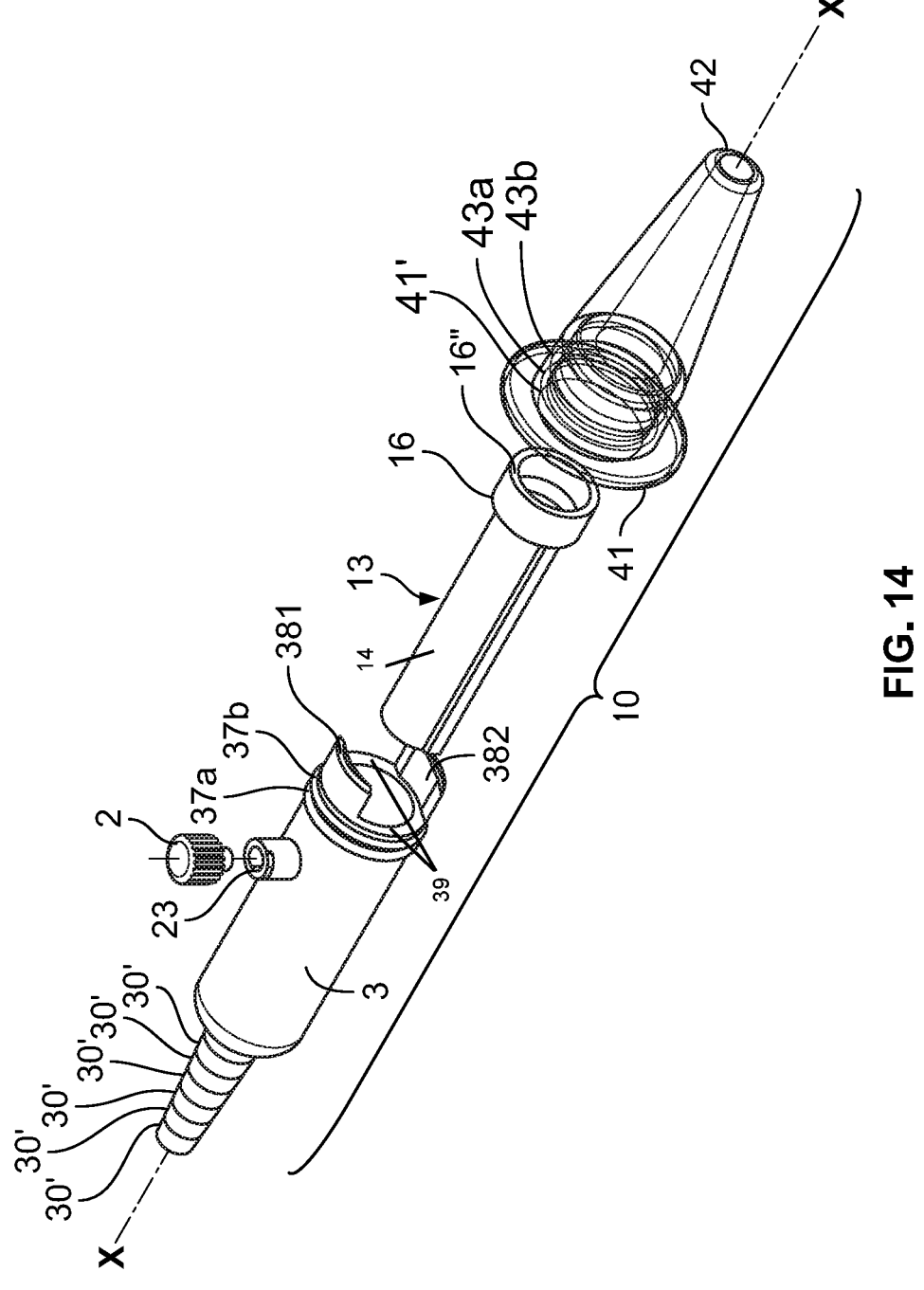
FIG. 14 illustrates an exploded view of the anatomical specimen collection device used in the anatomical specimen collection system of FIG. 1 in accordance with an embodiment of the present disclosure.

FIG. 11 illustrates another example of a Yankauer suction instrument 7. FIG. 12A illustrates an example of a Poole suction instrument 8a that may be used in place of the Frazier instrument 5 in any of the systems 100, 200, 300. FIG. 12B illustrates another Poole instrument 8b. FIG. 13 illustrates a more detailed view of a Frazier instrument 5. In embodiments, the proximal ends 7', 8a', 8b' and 5' include stepped outer surfaces that contact the inner surface of the opening in the proximal end 42 of the nozzle 4 for secure connection thereto.

In embodiments, other suction tool instruments and tips may be used in conjunction with the device 10. In embodiments, the flexible nature of the opening 42 at the distal end of the nozzle 4 allows it to receive a wide variety of instruments. In addition, the sequential, spaced apart configuration of the channels 43a, 43b and thread projections 37a, 37b provides a secure method of attaching the nozzle 4 to the body 3 and reduces the chances that the nozzle 4 will become separated from the body 3 when the Yankauer or Poole surgical suction instruments, or any other instruments, are installed onto the nozzle tip at distal end portion 42.

In embodiment, the body 3 has a tubular cross-section and configuration, however, other cross-sections such as triangular, square, rectangular, parallelogram, pentagonal, hexagonal, heptagonal, octagonal, etc. may be utilized.

Figure 15:
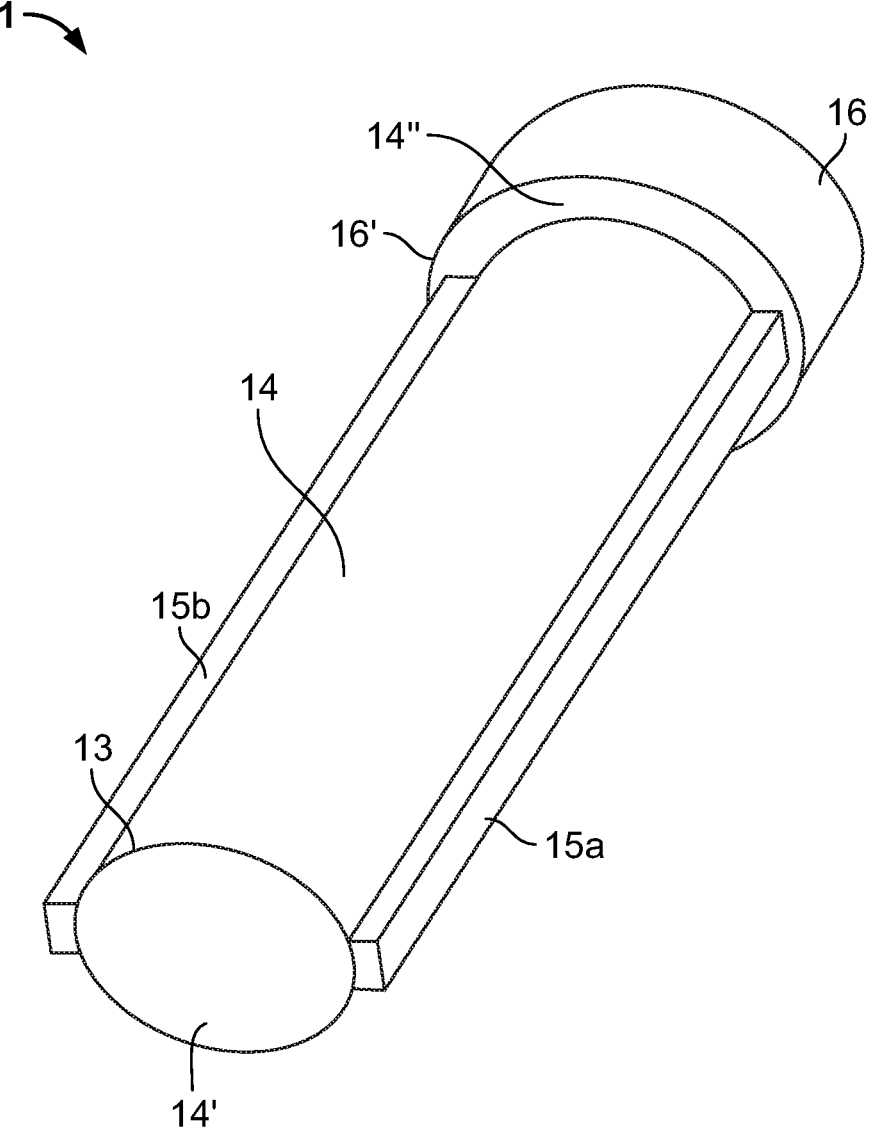
FIG. 15 is a more detailed view of a filter provided in the anatomical specimen collection device of FIG. 14.

FIG. 15 illustrates a more detailed view of the filter 1. As noted above, in embodiments, the filter 1 includes filter mesh 14 that is maintained in an extended cylindrical position by first and second alignment ribs 15a and 15b that are parallel to one another and extend orthogonally from toroidal surface 16' of cylindrical end supporting structure 16. In embodiments, the filter mesh 14 includes closed end 14' at a proximal end thereof. In embodiments, the perimeter 13 of the filter mesh portion 14 joins distal open end 14" and the cylindrical end supporting structure 16 to define distal open end 16" through which bone dust or other anatomical specimen is suctioned into the filter 1 during operation.

In embodiments, the filter 1 has a tubular cross-section and configuration, however, other cross-sections such as triangular, square, rectangular, parallelogram, pentagonal, hexagonal, heptagonal, octagonal, etc. may be utilized. In embodiments, the length of the filter 1 may be varied depending on the volume of specimen material to be collected.

In embodiments, the distal end portion 42 includes a tapered region 44 while the proximal end portion 41 includes a cylindrical region 45. In embodiments, both regions 44 and 45 have open ends to allow the passage of bone dust or other anatomical specimen through a distal end channel 44' in region 44 and through a proximal end channel 45' in region 45'.

In embodiments, following insertion of the filter mesh portion 14 of the filter 1 into the internal volume of space 35, the nozzle 4 is installed by the user onto the body 3 to engage the channels 43a, 43b with the thread projections 37a, 37b, respectively. The sequential, spaced apart configuration of the channels 43a, 43b and thread projections 37a, 37b provides a secure method of attaching the nozzle 4 to the body 3 to minimize inadvertent separation of the nozzle 4 from the body 3 and to maintain proper suction pressure during usage. The flexible nozzle 4 generally aligns with the longitudinal axis X-X of the body 3 and the filter 1.

In embodiments, distal end 42 of the nozzle is designed to allow fluid connection to the stepped connectors 7', 8a', 8b' and commonly found on standard suction instruments, e.g., the stepped connectors on the proximal ends of the Frazier 5, Yankauer 7' and Poole 8a, 8b suction instruments discussed above. In embodiments, the distal end 42 of the nozzle 4 is also configure such that it is suitable for patient contact and may be used to collect specimens directly via the nozzle aperture at distal end portion 42, depending on the preference of the surgeon.

In embodiments, the suction instruments have the stepped connectors or may have threads or other means for providing retention in the end portion 42 of the nozzle 4 of the collection device 10.

Figure 16:
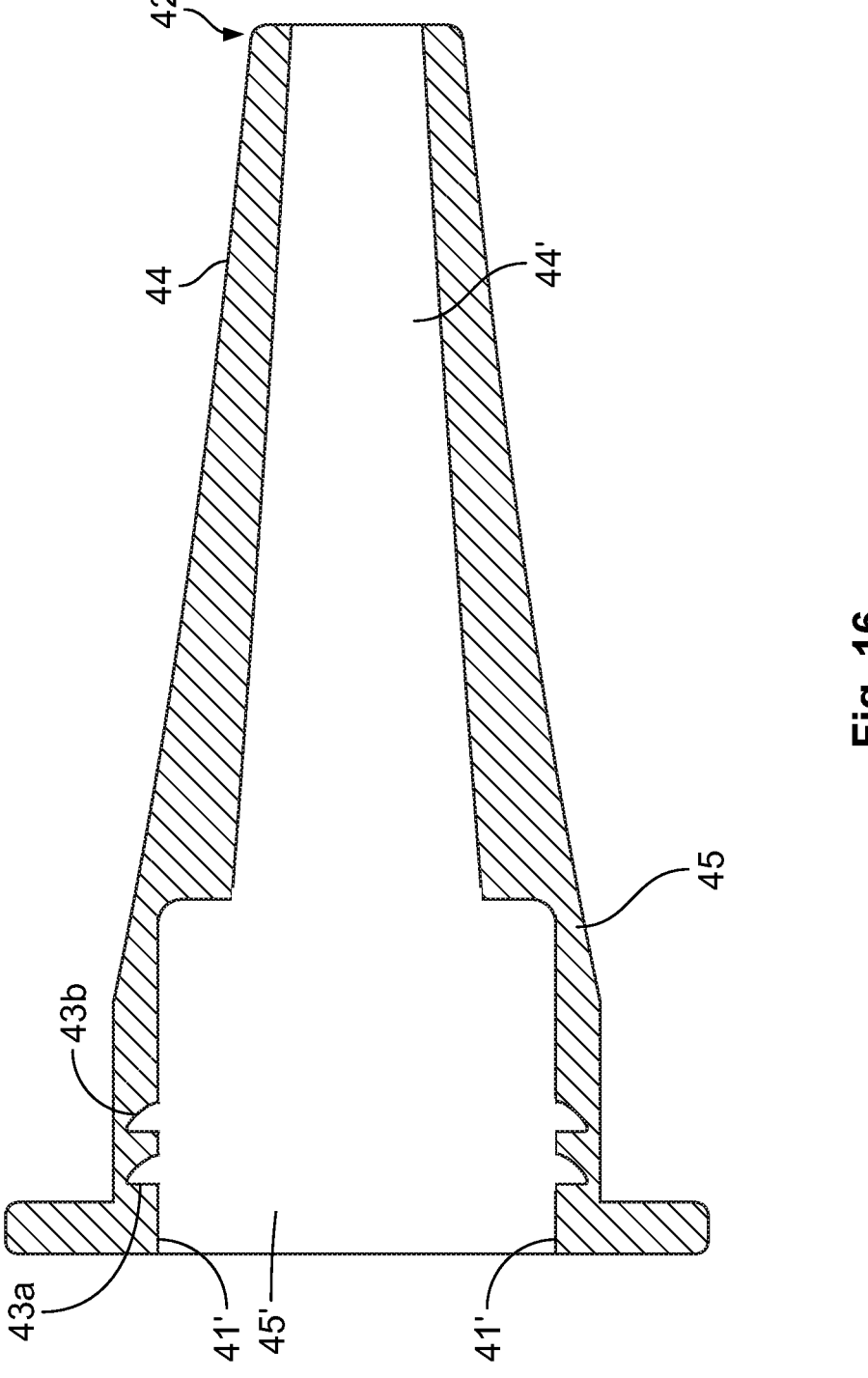
FIG. 16 is a cross sectional view of a nozzle element of the anatomical specimen collection device of FIG. 14.
Figure 17:
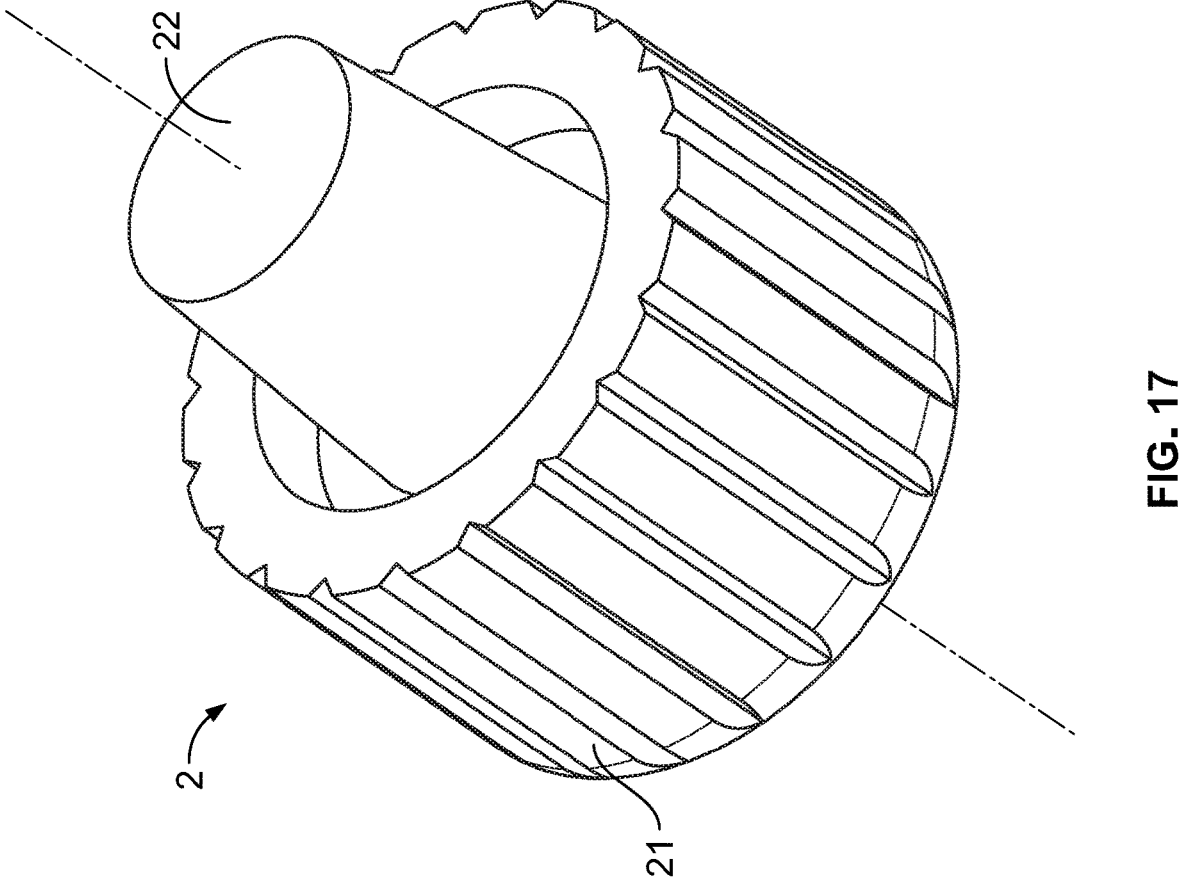
FIG. 17 illustrates an exemplary embodiment of a Luer cap suitable for use in the anatomical specimen collection device of FIG. 14.

FIG. 16 illustrates an exemplary embodiment of a Luer cap 2 that may be used to cover the port opening 23 in cylindrical wall 36 of the body 3 to seal the device 10 from the ambient air and vacuum. In embodiments, the cap 2 includes a stopper 22 that extends into the opening 23 and an outer grip portion 21 to allow for easy grip of the cap 2.

The body 3, nozzle 4 and filter 1 discussed and illustrated herein have certain dimensions, however, the device 10 and system 100, 200, 300 of the present disclosure are not limited to those dimensions. In embodiments, the body 3, nozzle 4 and filter 1 may be larger or smaller than illustrated and discussed herein, depending on the application for which they are being used. In embodiments, certain procedures may call for collection of more or less bone dust, another desired specimen, in which case, a larger or smaller device 10 may be used. For example, a lumbar fusion, or any fusion with multiple levels would require a fairly substantial amount of recovered bone dust. Large orthopedic reconstruction surgeries would also require a substantial amount of revered bone dust.

While several embodiments or aspects of the disclosure have been shown in the drawings, it is not intended that the disclosure be limited thereto, as it is intended that the disclosure be as broad in scope as the art will allow and that the specification be read likewise. Any combination of the above embodiments or aspects is also envisioned and is within the scope of the appended claims. Therefore, the above description should not be construed as limiting, but merely as exemplifications of particular embodiments or aspects. Those skilled in the art will envision other modifications within the scope of the claims appended hereto.

What is claimed is:

1. An anatomical specimen collection device comprising:
a hollow body extending along a longitudinal axis;
the body including:
a first opening in a proximal end thereof, the first opening surrounded by a flange extending in the proximal direction configured to provide a sealed connection to a suction source;
the first opening in fluid communication with an internal space;
a second opening at a distal end thereof; and
two opposed wall extensions extending in the distal direction from the distal end, wherein the two opposed wall extensions are spaced apart from each other to form a first annular gap and second annual gap between the two opposed wall extensions,
a pair of raised protrusions positioned adjacent the two opposed wall extensions on an outer surface of the body,
a filter mounted in the body between the first opening and the second opening:
the filter including:
a closed proximal end portion;
an open distal end portion including a cylindrical support element, the cylindrical support element having an outer diameter larger than that of the proximal end;
wherein the cylindrical support element is received between and entirely within the two opposed wall extensions such that the cylindrical support element does not extend distally or laterally beyond the two opposed wall extensions, is accessible via the first annular gap and the second annular gap; and
a mesh portion extending longitudinally between the closed proximal end portion and the open distal end portion defining an interior space aligned with the longitudinal axis; and
a flexible nozzle removably connected to the distal end of the body, the flexible nozzle tapering from a proximal end thereof in contact with the body to a distal end thereof, the distal end including a suction opening that is in fluid communication with the interior space of the filter and the first opening in the proximal end of the body such that anatomical specimen material is drawn into the suction opening, through the filter and the first opening when the first opening is connected to suction, wherein an inner surface of the proximal end of the nozzle includes a pair of channels positioned and configured to receive the pair of raised protrusions of the body to secure the nozzle to the body.

2. The anatomical specimen collection device of claim 1, wherein the mesh portion includes a mesh with a plurality of openings that are sized to allow blood and saline to pass through, while preventing bone dust from passing.

3. The anatomical specimen collection device of claim 1, wherein the filter further comprises two opposed ribs extending from the cylindrical support element to the closed proximal end of the filter and supporting the mesh of the mesh portion.

4. The anatomical specimen collection device of claim 1, wherein the filter is positioned such that there is a first gap between an outer perimeter of the filter and an internal surface of the body and a second gap between the closed proximal end portion of the filter and the proximal end of the body such that the first gap and the second gap are subject to negative pressure when the first opening of the body is connected to suction.

5. The anatomical specimen collection device of claim 1, wherein the nozzle is made of a flexible silicone material that is approved for contact with a patient's body.

6. The anatomical specimen collection device of claim 1, wherein the body further comprises a vent opening formed in the outer surface of the body near the distal end thereof.

7. The anatomical specimen collection device of claim 1, wherein an interior surface of the nozzle is flat such that the anatomical specimen material flows easily through the nozzle to the filter.

8. The anatomical specimen collection device of claim 1, wherein the suction opening of the nozzle has a smaller diameter than the proximal end of the nozzle.

9. The anatomical specimen collection device of claim 1, wherein the suction opening is flexible.

10. An anatomical specimen collection system comprises:
a suction tube configured for connection to a suction supply; and
an anatomical specimen collection device in fluid communication with the section tube, the anatomical specimen collection device including:
a hollow body extending along a longitudinal axis;
the body including:
a first opening in a proximal end thereof, the first opening surrounded by a flange extending in the proximal direction configured to provide a sealed connection to the suction tube;
the first opening in fluid communication with an internal space;
a second opening at a distal end thereof; and
two opposed wall extensions extending in the distal direction, wherein the two opposed wall extensions are spaced apart from each other to form a first annular gap and second annual gap between the two opposed wall extensions;
a pair of raised protrusions positioned adjacent the two opposed wall extensions on an outer surface of the body;
a cylindrical filter mounted in the body between the first opening and the second opening:
the cylindrical filter including:
a closed proximal end portion;
an open distal end portion including a cylindrical support element;
wherein the cylindrical support element is received between and entirely within the two opposed wall extensions such that the cylindrical support element does not extend distally or laterally beyond the two opposed wall extensions and is accessible via the first annular gap and the second annular gap; and a mesh portion extending longitudinally between the closed proximal end portion and the open distal end portion defining a cylindrical interior space aligned with the longitudinal axis, wherein a gap is provided between an outer surface of the filter and an inner surface of the body wherein the gap has a uniform shape between the cylindrical support element and the closed proximal end portion such that a space between the outer surface of the filter and the inner surface of the body is substantially uniform in size; and a flexible nozzle removably connected to the distal end of the body, the flexible nozzle tapering from a proximal end thereof in contact with the body to a distal end thereof, the distal end including a suction opening that is in fluid communication with the interior space of the filter and the first opening in the proximal end of the body such that anatomical specimen material is drawn into the suction opening, through the filter and the first opening when suction is applied via the suction tube through the first opening, wherein the suction tube is connected to the proximal end of the body, wherein an inner surface of the proximal end of the nozzle includes a pair of channels positioned and configured to receive the pair of raised protrusions of the body to secure the nozzle to the body.

11. The anatomical specimen collection system of claim 10 further comprising a hollow suction instrument connected to the suction opening of the nozzle and including a distal end configured for contact with a patient to provide the anatomical specimen material to the anatomical specimen collection device.

12. The anatomical specimen collection system of claim 11, wherein the proximal end of the hollow suction instrument includes a stepped outer surface that is received in the suction opening of the anatomical specimen collection device to connect the instrument to the anatomical specimen collection device.

13. The anatomical specimen collection system of claim 11, wherein an interior surface of the suction opening is smooth such that anatomical specimen material flows freely into the anatomical specimen collection device.

14. The anatomical specimen collection system of claim 11, wherein the hollow suction instrument is one of a Frazier instrument, a Poole instrument, and a Yankauer instrument.

15. The anatomical specimen collection system of claim 10, further comprising:

an adaptor element including:
    a proximal end that is received in the suction opening of the nozzle; and
    a distal end; and
a second suction tube with a proximal end connected to the distal end of the adaptor and a distal end connected to a hollow suction instrument such that the anatomical specimen material is collected by the hollow suction instrument and passes through the second suction tube, through the adaptor element and into the anatomical specimen collection device through the suction opening.

16. The anatomical specimen collection system of claim 15, wherein the hollow suction instrument is one of a Frazier instrument, a Poole instrument, and a Yankauer instrument.

* * * * *